(12) United States Patent
Zinn et al.

(10) Patent No.: US 9,782,575 B2
(45) Date of Patent: Oct. 10, 2017

(54) ADJUSTABLE-LENGTH DUAL-LUMEN HEMODIALYSIS CATHETER AND A METHOD FOR ITS USE

(71) Applicants: Kenneth M. Zinn, Westport, CT (US); Mark Steven Fisher, Sellersville, PA (US)

(72) Inventors: Kenneth M. Zinn, Westport, CT (US); Mark Steven Fisher, Sellersville, PA (US)

(*) Notice: Subject to any disclaimer, the term of this patent is extended or adjusted under 35 U.S.C. 154(b) by 909 days.

(21) Appl. No.: 13/691,988

(22) Filed: Dec. 3, 2012

(65) Prior Publication Data

US 2014/0155801 A1    Jun. 5, 2014

(51) Int. Cl.
| | |
|---|---|
| *A61M 25/02* | (2006.01) |
| *A61M 39/10* | (2006.01) |
| *A61M 25/00* | (2006.01) |
| *A61M 1/36* | (2006.01) |
| *A61M 39/02* | (2006.01) |
| *A61M 39/08* | (2006.01) |

(52) U.S. Cl.
CPC ...... *A61M 39/1011* (2013.01); *A61M 1/3661* (2014.02); *A61M 25/0097* (2013.01); *A61M 39/0247* (2013.01); *A61M 2025/0031* (2013.01); *A61M 2025/0286* (2013.01); *A61M 2039/0258* (2013.01); *A61M 2039/0261* (2013.01); *A61M 2039/0273* (2013.01); *A61M 2039/0282* (2013.01); *A61M 2039/087* (2013.01)

(58) Field of Classification Search
CPC ............ A61M 1/3661; A61M 16/0434; A61M 25/0029; A61M 25/0097; A61M 39/1011; A61M 2025/0034

USPC ......................................... 604/6.16, 43, 534
See application file for complete search history.

(56) References Cited

U.S. PATENT DOCUMENTS

| | | | | |
|---|---|---|---|---|
| 5,129,891 A | * | 7/1992 | Young ............... | A61M 39/0208 285/238 |
| 2002/0107506 A1 | * | 8/2002 | McGuckin, Jr. ...... | A61M 1/285 604/523 |
| 2003/0093027 A1 | * | 5/2003 | McGuckin, Jr. ...... | A61M 1/285 604/6.16 |
| 2003/0093029 A1 | * | 5/2003 | McGuckin, Jr. ...... | A61M 1/285 604/43 |
| 2004/0193119 A1 | * | 9/2004 | Canaud ............... | A61M 1/3661 604/247 |
| 2008/0045894 A1 | * | 2/2008 | Perchik ............. | A61M 25/0194 604/96.01 |
| 2008/0108969 A1 | * | 5/2008 | Kerr ................... | A61M 1/3653 604/500 |
| 2008/0306465 A1 | * | 12/2008 | Bailey ............... | A61M 25/0029 604/500 |

(Continued)

*Primary Examiner* — Gerald Landry, II
(74) *Attorney, Agent, or Firm* — Muskin & Farmer, LLC

(57) ABSTRACT

The present adjustable-length dual-lumen hemodialysis catheter can eliminate the need to stock various lengths of hemodialysis catheters and can provide a hemodialysis catheter, which can be trimmed to various lengths in order to precisely accommodate patients of various shapes and sizes. Specifically, the present adjustable-length dual-lumen hemodialysis catheter can comprise a cuff ring assembly, which can be secured at selected locations along the trailing limbs of the catheter allowing the cuff ring assembly to be installed in a location chosen to precisely fit a particular patient.

6 Claims, 8 Drawing Sheets

(56) References Cited

U.S. PATENT DOCUMENTS

| | | | |
|---|---|---|---|
| 2010/0191165 A1* | 7/2010 | Appling | A61M 25/0009 604/6.16 |
| 2010/0228178 A1* | 9/2010 | McGraw | A61M 1/3653 604/6.16 |
| 2011/0301522 A1* | 12/2011 | DeFonzo | A61M 1/3653 604/6.16 |
| 2012/0209206 A1* | 8/2012 | Scandone, Jr. | A61M 25/04 604/175 |

* cited by examiner

ADJUSTABLE-LENGTH DUAL-LUMEN HEMODIALYSIS CATHETER AND A METHOD FOR ITS USE

FIELD OF THE INVENTION

The present general inventive concept is directed toward a dual-lumen catheter apparatus such as those commonly used to perform hemodialysis.

BACKGROUND

Catheters are tubes used in the medical field to be inserted into a patient allowing for the drainage of, or administration of fluids and medicines. Specifically, dual-lumen hemodialysis catheters are a class of catheter, which can be used to exchange blood to and from a hemodialysis machine and a patient suffering from renal failure. These catheters are typically placed in a large vein of a patient, usually the jugular vein, and advanced down toward the chest in a retrograde insertion or tunneled through the subcutaneous tissue of the upper chest and into a large vein in an antegrade insertion. Current hemodialysis catheters can be split at their distal ends, and these catheters are referred to as 'split-tip catheters.' The free-floating ends of such catheters can provide better flow rates and prevent clogging of the catheter. Existing hemodialysis catheters are secured to the patient through a fixed hub and suture wing assembly, intended to reduce the risk of accidental dislodgement from the patient. In order to install these catheter correctly, they must be manufactured in various lengths to adequately fit the dimensions of patients of various shapes and sizes, which requires hospitals and clinics to stock various lengths of hemodialysis catheters. Keeping such an inventory can be both costly and difficult to maintain.

What is needed is an adjustable-length hemodialysis catheter, which can be adapted to fit nearly any patient, regardless of that patient's size or shape, thus eliminating the need for hospitals or other healthcare facilities to stock multiple lengths of hemodialysis catheters.

SUMMARY OF THE INVENTION

It is an aspect of the present device to provide an improved dual-lumen hemodialysis catheter that can be manually adjusted to a desired length to fit an individual patient's particular size and shape. It is another aspect of the present device to provide a method for placing and properly installing this improved hemodialysis catheter into a patient.

This aspect can be obtained by a dual-lumen hemodialysis catheter apparatus comprising: a cuff ring assembly comprising: a cuff ring further comprising a locking section comprising at least one cuff ring wedge-mounting hole; a cuff ring wedge comprising at least one cuff ring wedge peg configured to be securely connected within the locking section; a cuff; and a dual-lumen hemodialysis catheter comprising a first end and a second end, wherein the second end comprises two trailing limbs.

These together with other aspects and advantages, which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Further features and advantages of the present device, as well as the structure and operation of various embodiments of the present device, will become apparent and more readily appreciated from the following description of the preferred embodiments, taken in conjunction with the accompanying drawings of which.

DESCRIPTION OF THE PREFERRED EMBODIMENTS

Figure 1A:
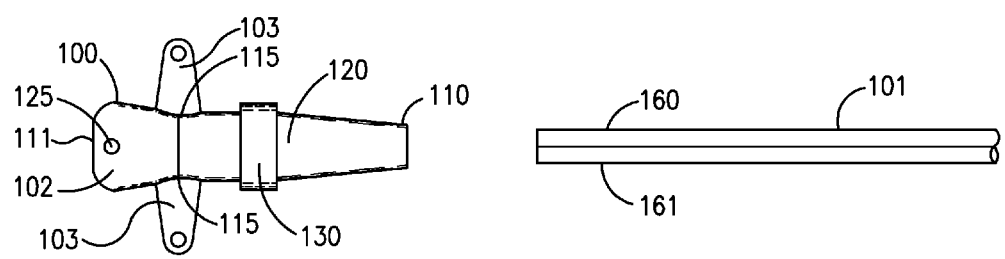
FIG. 1A is a top view drawing of a cuff ring assembly and the proximal end of a dual-lumen hemodialysis catheter, according to an embodiment.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Reference will now be made in detail to the presently preferred embodiments of the invention, examples of which are illustrated in the accompanying drawings, wherein like reference numerals refer to like elements throughout.

The present concept relates to dual-lumen hemodialysis catheters having lengths that can be adjusted to fit patients of various sizes and dimensions. More specifically, the present concept relates to a dual-lumen hemodialysis catheter comprising an adjustable cuff ring assembly, which can be used to adjust the length of the proximal end of the catheter. The present catheter can comprise a distal end, or leading end, and a proximal end, or trailing limb, wherein the leading end can be placed within a large vein in the patient and the trailing limb can extend outside the patient, typically through an incision in the patient's chest. The leading end can comprise a step-tip design, a split-tip design, a spiral-z tip design or any other suitable leading end comprising a dual-lumen catheter. However, the split-tip design may be currently preferable over the step-tip design because openings in the intravascular portion of the split-tip design have been shown to be less prone to clogging than those comprising the step-tip design.

The present catheter can comprise a segment of permanent adhesion, between its leading end and its trailing limb, wherein one half of the dual-lumen catheter cannot be split apart from the other half, thus preventing the limbs of the catheter from being split completely into two individual catheters. In an embodiment, the two limbs comprising the catheter can each be D-shaped, wherein a flat side of the D of a first limb can connect to a flat side of the D of a second limb and a cross-section of the two limbs together can form either the shape of a circle or oval. However, any other suitable shape of catheter limbs can also be used.

In an embodiment, the present dual-lumen hemodialysis catheter can comprise a cuff ring assembly configured to secure the varying lengths of the trailing limbs of the catheter to the cuff ring assembly and can also be configured to allow the cuff ring assembly to be securely connected to a patient. This cuff ring assembly can comprise a cuff ring, which can be a hollow tube having a first opening at a bottom end and a second opening at a top end. This cuff ring can be configured to allow the trailing limbs of the catheter to be placed through the cuff ring by threading the trailing limbs in through the first opening and out through the second opening. The bottom end of the cuff ring can be tapered to allow it to be inserted into an incision in the patient's chest through which the trailing limbs of the catheter have been extended. In an embodiment, one or more suture wings can extend from one or more sides of the cuff ring, wherein each suture wing can be used to secure the cuff ring and the entire cuff ring assembly externally to a patient's body by suturing each suture wing to the patient's skin. In an embodiment, the cuff ring assembly can also comprise a cuff, made from a material such as Dacron, which can be configured to slide over the tapered bottom end of the cuff ring. In an embodiment, this cuff can be placed manually along the cuff ring so that a patient's subcutaneous tissue can be allowed to grow into the cuff, enabling the catheter to be secured inside the patient's body and the risk of infection can thus be reduced.

In an embodiment, the present device can also comprise a cuff ring wedge that can be inserted into the top end of the cuff ring comprising the cuff ring assembly. This cuff ring wedge can be placed between the two trailing limbs of the dual-lumen catheter, pressing each trailing limb against an inner surface of the cuff ring, thus locking each trailing limb into a fixed position relative to the cuff ring. In an embodiment, the top end of the cuff ring can be configured to contain the cuff ring wedge along with both trailing limbs and the top end of the cuff ring can be configured to securely connect the cuff ring wedge into the second opening of the cuff ring. Although the cuff ring wedge is shown as having only flat sides, the shape of the cuff ring wedge can be configured to secure various shapes of catheters to the cuff ring. After the trailing limbs of the dual-lumen catheter have been securely connected to the cuff ring, each of the trailing limbs can be trimmed to any desired length and hub assemblies, comprising clamps and hubs, can be connected to each of the trailing limbs of the catheter.

In an embodiment, the present device can be used in conjunction with a method wherein the leading end of the catheter can be positioned within a large vein in a patient, usually the aorta or superior vena cava, and the trailing limb can then be retrograde tunneled back through a subcutaneous tract and emerge from a skin exit site, typically located on the surface of the patient's chest. The trailing limb of the catheter can be split down to a selected location, which can ordinarily be located one (1) to two (2) centimeters within the subcutaneous tunnel. The trailing limbs of a dual-lumen catheter can be threaded through the cuff ring assembly, including at least one suture wing, until the suture wings are located adjacent to the skin exit site. The manual positioning of the cuff ring assembly can allow the cuff ring to be placed subcutaneously over the dual-lumen catheter at an appropriate selected location within the patient. The cuff can be placed so as to allow subcutaneous tissue to grow into the cuff, thus facilitating the proper connection of the catheter to the patient's skin at the exit site. The suture wing can allow the cuff ring assembly to be secured to the patient's skin with sutures at a chosen location. Each suture wing can restrict movement of the cuff ring assembly relative to the patient. The trailing limbs of the dual-lumen catheter can then be trimmed to a desired length to accommodate the patient's size and dimensions, allowing for an adjustable-length dual-lumen hemodialysis catheter. Finally, protective clamps and hub locks can be attached to the trailing limbs of the dual-lumen hemodialysis catheter according to standard practice.

In an embodiment, a ribbed cuff ring wedge can be inserted into the cuff ring, between the two trailing limbs, and can be secured within the top end of the cuff ring by connecting to it. The cuff ring wedge can lock the trailing limbs in place, thus reducing risk of entanglement and dislodgement of the catheter from the patient.

In an embodiment, the present cuff ring can be made from a soft material that can prevent the splitting of the catheter if tension is applied to the catheter. In an embodiment, the present cuff ring wedge can be made of a material, which can be slightly harder than the material comprising the cuff ring that can act to lock the trailing limbs of the catheter in place. The softer material comprising the cuff ring can also be configured to stretch in order to accommodate the insertion of the harder wedge, into the cuff ring.

FIG. 1A is a top view drawing of a cuff ring assembly 100 and the proximal end of a dual-lumen hemodialysis catheter 101, according to an embodiment.

In an embodiment, a cuff ring assembly 100, as depicted in FIG. 1A, can comprise a hollow, cylindrical tube, referred to as a cuff ring 120, comprising a bottom end 110 and a top end 111, wherein the cuff ring 120 near the bottom end 110 can be tapered so that its circumference and width is smallest at the bottom end 110, and the top end 111 can comprise a wider locking section 102. One or more suture wings 103 can be connected to sides 115 near the top end 111 of the cuff ring 120. In an embodiment, one or more suture wings 103 can comprise a cuff ring 120 made from a single piece of material. The cuff ring assembly 100 can be manually installed in a desired location on a patient so as to place the bottom end 110 of the cuff ring 120 and a cuff 130 into a subcutaneous tunnel (not shown in FIG. 1) within the patient. The suture wing 103 can be placed externally near the exit site of the subcutaneous tunnel (not shown in FIG. 1A), and trailing limbs 160 and 161 of the proximal end of the dual-lumen hemodialysis catheter 101 can be placed through the bottom end 110 of the cuff ring 120. The cuff ring 120 can comprise a hollow, cylindrical tube having a locking section 102 comprising an enlarged opening at the top end 111. In an embodiment, the locking section 102 can also comprise a first cuff ring wedge-mounting hole 125 located near the top end 111 of the cuff ring 120. In an embodiment, a second cuff ring wedge-mounting hole (not visible in FIG. 1A) can be located opposite the first cuff ring wedge-mounting hole 125 and can be used to connect a cuff ring wedge (not shown in FIG. 1A) to the cuff ring 120.

Figure 1B:
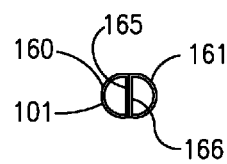
FIG. 1B is a cross-sectional view of the proximal end of a dual-lumen hemodialysis catheter.

FIG. 1B is a cross-sectional view of the trailing limbs 160 and 161 of a dual-lumen hemodialysis catheter 101.

Each of the trailing limbs depicted in FIG. 1B are D-shaped, but the present invention can be configured to be used with limbs of various shapes and sizes. In an embodiment a flat side 165 comprising trailing limb 160 can be removably connected to flat side 166 comprising trailing limb 161, wherein each limb can be initially connected to the other, but can be configured to be easily pulled apart (separated) without damaging either limb 160 or 161.

Figure 2:
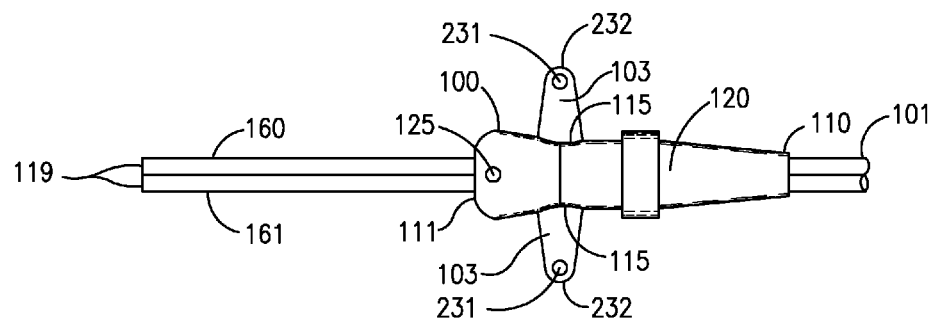
FIG. 2 is a top view drawing of a cuff ring assembly, wherein two trailing limbs of the proximal end of a dual-lumen hemodialysis catheter have been threaded through the cuff ring assembly, according to an embodiment.

FIG. 2 is a top view drawing of a cuff ring assembly 100, wherein two trailing limbs 160 and 161 of the proximal end of the dual-lumen hemodialysis catheter 101 have been threaded through the cuff ring assembly 100, according to an embodiment.

In an embodiment, the trailing limbs 160 and 161 of a dual-lumen hemodialysis catheter 101 can be threaded through the cuff ring 120 by placing the tips 119 of the trailing limbs 160 and 161 into the cuff ring 120 through the bottom end 110 first then out through the top end 111 of the cuff ring 120. The cuff ring assembly 100 can be moved over the trailing limbs 160 and 161 of the proximal end of the dual-lumen hemodialysis catheter 101 until the bottom end 110 of the cuff ring 120, can be inserted into the exit site and into the subcutaneous tunnel (not shown in FIG. 2).

In an embodiment, each suture wing 103 can be a wing-shaped protrusion on either side 115 of the cuff ring 120 near the top end 111 and the suture wing 103 can be placed on either side 115 of the cuff ring 120. The suture wing 103 can also comprise one or more suture wing holes 231, which can be located at the outermost end 232 of each suture wing 103 according to an embodiment. These suture wing holes 231 can be used to secure the cuff ring 120 to a patient's skin, and into the subcutaneous tunnel, at a desired location near the exit site of the subcutaneous tunnel using sutures (the patient, the exit site and the sutures are not shown in FIG. 2).

Figure 3:
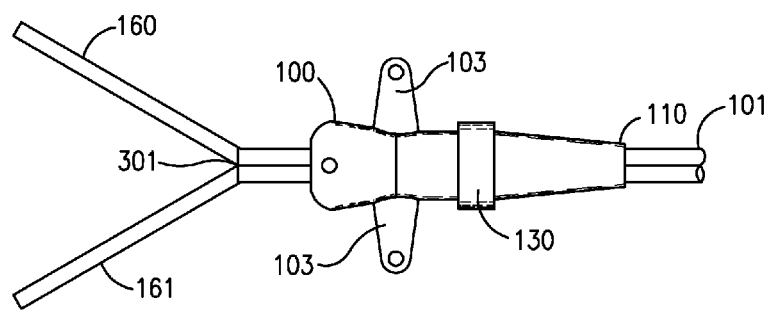
FIG. 3 is a top view drawing of a cuff ring assembly, wherein two trailing limbs of the dual-lumen hemodialysis catheter have been threaded through the cuff ring assembly, and the two trailing limbs have been split apart to a selected location along the dual-lumen hemodialysis catheter, according to an embodiment.

FIG. 3 is a top view drawing of a cuff ring assembly 100, wherein two trailing limbs 160 and 161 of the proximal end of the dual-lumen hemodialysis catheter 101 have been threaded through the cuff ring assembly 100, and the two trailing limbs 160 and 161 have been split apart to a selected location 301 along the dual-lumen hemodialysis catheter 101, according to an embodiment.

In an embodiment, the cuff 130 can be placed at a desired location under a patient's skin (not shown in FIG. 3), and the suture wings 103 can be used to secure the cuff ring assembly 100 externally to the patient's skin, near the exit site of the subcutaneous tunnel (not shown in FIG. 3). The cuff ring assembly 100 can comprise a cuff 130, which can be a hollow ring made from a plastic material, or a similar suitable material known to those skilled in the art of medical devices. This cuff 130 can be placed subcutaneously into the patient (not shown in FIG. 3) so as to secure the proximal end of the dual-lumen hemodialysis catheter 101 into the subcutaneous tissue by permitting tissue ingrowth around its entire circumference, which also adds a barrier to infection.

Figure 4:
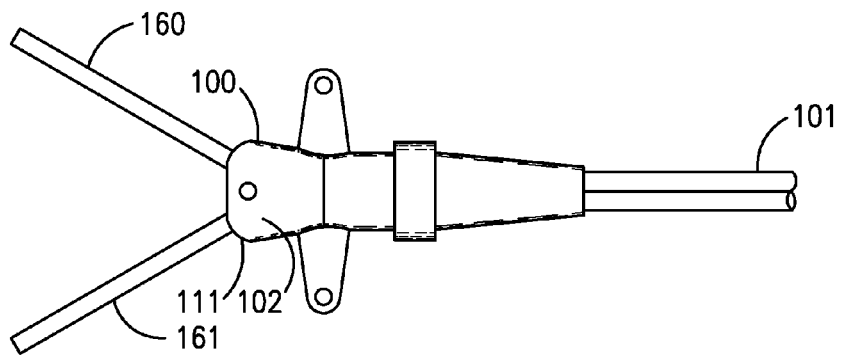
FIG. 4 is a top view drawing of a cuff ring assembly, wherein two trailing limbs of the proximal end of a dual-lumen hemodialysis catheter have been threaded through the cuff ring assembly, and the two trailing limbs have been split apart to a selected location (not visible in FIG. 4) and this location is located within the locking section of the cuff ring assembly, according to an embodiment.

FIG. 4 is a top view drawing of a cuff ring assembly 100, wherein two trailing limbs 160 and 161 of the proximal end of the dual-lumen hemodialysis catheter 101 have been threaded through the cuff ring assembly 100, and the two trailing limbs 160 and 161 have been split apart to a selected location (not visible in FIG. 4) and this location is located within the locking section 102 of the cuff ring assembly, according to an embodiment.

In an embodiment, the selected location 301 where the trailing limbs 160 and 161 are split apart can be located just inside the top end 111 of the locking section 102 of the cuff ring assembly 100. This selected location 301 can also be located one (1) to two (2) centimeters inside the subcutaneous tunnel (not shown in FIG. 4). The ability to adjust the position of this selected location 301 to many different locations along the proximal end of the dual-lumen hemodialysis catheter 101 can allow for the precise placement of the cuff ring assembly 100 in relation to the proximal end of the dual-lumen hemodialysis catheter 101. The trailing limbs 160 and 161 are initially connected together but the trailing limbs 160 and 161 can be separated manually. As will become apparent, this aspect of the present device can allow the dual-lumen hemodialysis catheter 101 to be very finely adjusted to fit patients of a wide variety of sizes and shapes, thus ensuring a proper fit while maintaining proximal tip location at the desired position.

Figure 5A:
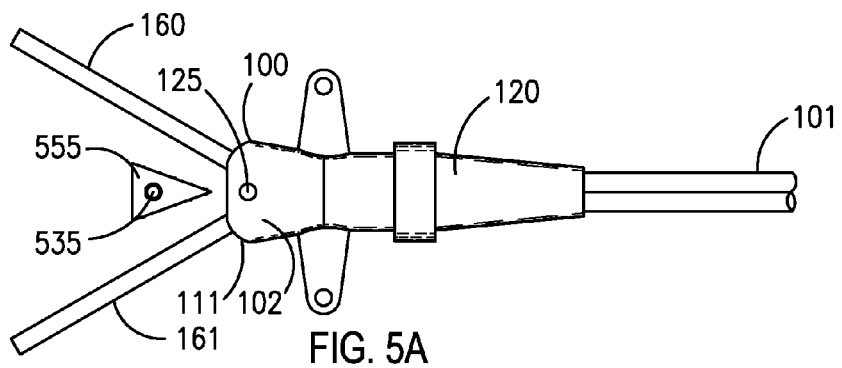
FIG. 5A is a top view drawing of a cuff ring assembly, wherein two trailing limbs of the proximal end of a dual-lumen hemodialysis catheter have been threaded through the cuff ring assembly, and the two trailing limbs have been split apart to a selected location (not visible in FIG. 5A) and this location is located within the locking section of the cuff ring assembly and a cuff ring wedge has been placed near the top end of the locking section and between the trailing limbs at the location, according to an embodiment.

FIG. 5A is a top view drawing of a cuff ring assembly 100, wherein two trailing limbs 160 and 161 of the proximal end of a dual-lumen hemodialysis catheter 101 have been threaded through the cuff ring assembly 100, and the two trailing limbs 160 and 161 have been split apart to a selected location (not visible in FIG. 5A) and this location is located within the locking section 102 of the cuff ring assembly 100 and a cuff ring wedge 555 has been placed near the top end 111 of the locking section 102 and between the trailing limbs 160 and 161 at the selected location, according to an embodiment. The cuff ring wedge 555 has two pegs 535 and 545 (see FIG. 5B) configured to connect the cuff ring wedge 555 to the locking section 102.

Figure 8:
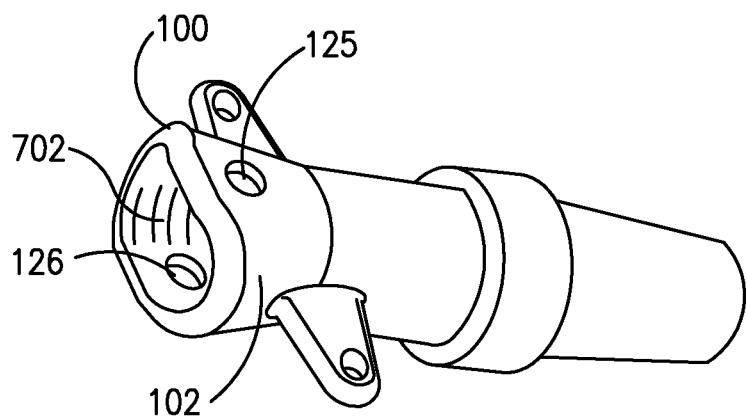
FIG. 8 is a perspective view drawing showing the rear, top and side of a cuff ring assembly, not comprising a cuff ring wedge, according to an embodiment.

In an embodiment, the cuff ring wedge 555 can be inserted into the top end 111 of the locking section 102 and securely connected to, and within, the locking section 102 by placing at least one cuff ring wedge peg 535 into a first cuff ring wedge-mounting hole 125, and preferably each cuff ring peg, 535 and 545, can be placed in into each cuff ring wedge-mounting hole, 125 and 126, (A second cuff ring wedge-mounting hole 126 can be viewed in FIG. 8.). Although only a peg and hole system for securely connecting the cuff ring wedge 555 to the locking section 102 is shown in the attached figures, the cuff ring wedge 555 can be similarly connected to the cuff ring 120 using any number of alternative suitable connecting devices known in the art (e.g., friction fit, snap, etc.) One function of the cuff ring wedge 555 is to secure each of the trailing limbs 160 and 161 of the dual-lumen hemodialysis catheter 101 to the locking section 102 of the cuff ring 120 by pressing the trailing limbs 160 and 161 against inner walls (not visible in FIG. 5A) of the locking section 102.

In an embodiment, the first cuff ring peg 535, comprising the cuff ring wedge 555, can be configured to fit within the first cuff ring wedge-mounting hole 125 in the cuff ring 120 and the first cuff ring peg 535 can snap into the first cuff ring wedge-mounting hole 125 to secure the cuff ring wedge 555 into the locking section 102 of the cuff ring 120. The second cuff ring peg 545 (not visible in FIG. 5A) can also snap into the second cuff ring wedge-mounting hole 126 (not visible in FIG. 5A). The cuff ring wedge 555 can be located between the two trailing limbs 160 and 161 of the catheter, allowing the trailing limbs 160 and 161 to each extend out separately from the top end 111 of the cuff ring assembly 100. The cuff ring wedge 555 can securely connect the two trailing limbs 160 and 161 to the cuff ring assembly 100 so that they are held apart, making them less likely to become tangled.

Figure 5B:
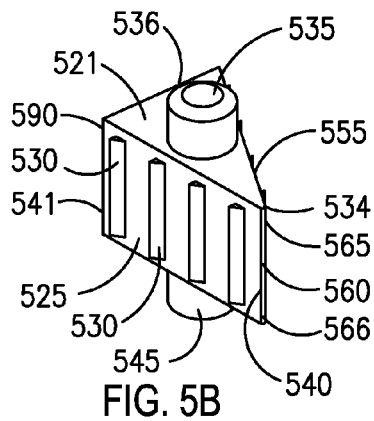
FIG. 5B is a perspective view drawing showing the top, front and side of a cuff ring wedge, according to an embodiment.

FIG. 5B is a perspective view drawing showing the top, front and side of a cuff ring wedge 555, according to an embodiment.

In an embodiment, the cuff ring wedge 555 can be wedge-shaped, comprising a top triangular flat side 521, having a narrow front end 534 and a wide back end 536, and a bottom triangular flat side (not visible in FIG. 5B), also having a narrow front end and a wide back end, identical to the top triangular flat side 521. The cuff ring wedge 555 can also comprise a first tapered side 525, having a first end 540 and a second end 541 and a second tapered side (only partially visible in FIG. 5B but appears identical to the first tapered side 525) opposite the first tapered side 525, also having a first end and a second end (not visible in FIG. 5B). Wherein, the first end 540 of the first tapered side 525 and the first end of the second tapered side can connect to form a blade end 560 of the cuff ring wedge 555, having a top blade side 565 and a bottom blade side 566 and the narrow front end 534 of the top triangular flat side 521 can be connected to the top blade side 565 and the bottom triangular flat side can be connected to the bottom blade side 566. In an embodiment, the cuff ring wedge can also comprise a back side 590 (not visible in FIG. 5B, but visible in FIG. 7B) which can be flat, the back side 590 being opposite the blade side 560 and can connect to the wide back end 536 of the top triangular flat side 521 and the wide back end (not visible in FIG. 5B) of the bottom triangular flat side (not visible in FIG. 5B) as well as the second end 541 of the first tapered side 525 and the second end of the second tapered side (not visible in FIG. 5B but can be structured identically to the first tapered side 525). In an embodiment, the outer surface of the first tapered side 525 and the outer surface of the second tapered side can comprise ribs, barbs 530 or other surface designs configured to increase friction, which can allow the cuff ring wedge 555 to more effectively grip the trailing limbs 160 and 161 of the dual-lumen hemodialysis catheter 101.

In an embodiment, a first peg 535 can be connected to the top triangular flat side 521 and a second peg 545, which can be identical to first peg 535, can be connected to the bottom triangular flat side (not visible in FIG. 5B but looks identical to top triangular flat side 521) opposite the first peg 535. As mentioned above, the first peg 535 can be configured to fit within the first cuff ring wedge-mounting hole 125 and the second peg 545 can be configured to simultaneously fit within a second cuff ring wedge-mounting hole 126, which is not visible in FIG. 5, but is visible in FIG. 8. When these pegs 535 and 545 are secured within their respective cuff ring wedge mounting holes 125 and 126 the cuff ring wedge 555 can be secured within the locking section 102 of the cuff ring assembly 100. In an embodiment, the cuff ring wedge 555 can be made from a harder, less flexible material than that comprising the cuff ring 120.

Figure 6:
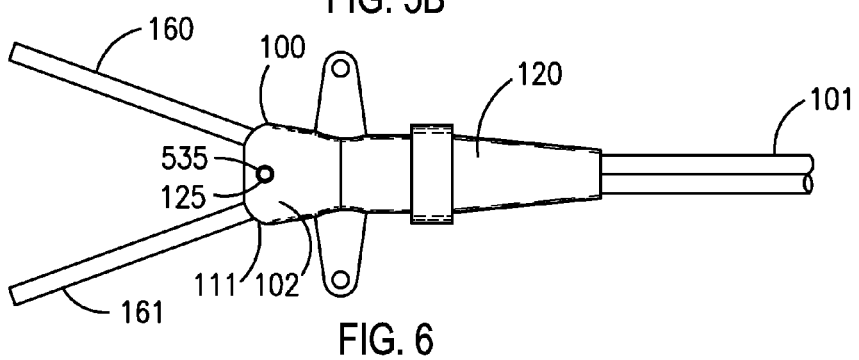
FIG. 6 is a top view drawing of a cuff ring assembly, wherein two trailing limbs of the proximal end of a dual-lumen hemodialysis catheter have been threaded through the cuff ring assembly, and the two trailing limbs have been split apart to a selected location (not visible in FIG. 6) and this location is located within the locking section of the cuff ring assembly and a cuff ring wedge (not visible in FIG. 6) has been placed into the top end of the locking section and between the trailing limbs at the location, thus securing the two trailing limbs to the cuff ring assembly, according to an embodiment.

FIG. 6 is a top view drawing of a cuff ring assembly 100, wherein two trailing limbs 160 and 161 of the dual-lumen hemodialysis catheter 101 have been threaded through the cuff ring assembly 100, and the two trailing limbs 160 and 161 have been split apart to a selected location (not visible in FIG. 6) and this location is located within the locking section 102 of the cuff ring assembly 100 and a cuff ring wedge (not visible in FIG. 6) has been placed into the top end 111 of the locking section 102 and between the trailing limbs 160 and 161 at the location, thus securing the two trailing limbs 160 and 161 to the cuff ring assembly 100, according to an embodiment.

In this view the first peg 535 can be seen within the first cuff ring wedge-mounting hole 125, indicating that the cuff ring wedge 555 has been securely connected to the locking section 102, thereby also securely connecting the trailing limbs 160 and 161 of the dual-lumen hemodialysis catheter 101 to the locking section 102 of the cuff ring assembly 100. The second peg 545 (not visible in FIG. 6) can be inserted into the second cuff ring wedge-mounting hole 126 (not visible in FIG. 6) located directly opposite the first cuff ring wedge-mounting hole 125.

Figure 7A:
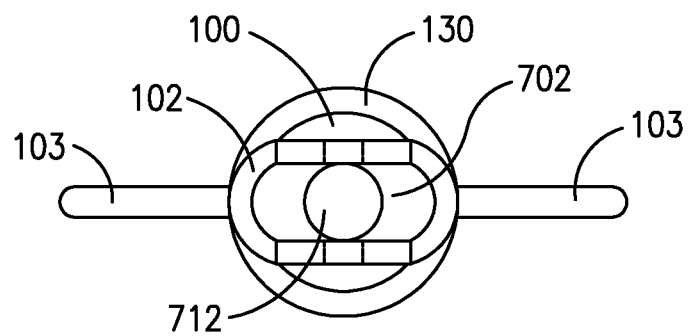
FIG. 7A is a rear view drawing of a cuff ring assembly not comprising a cuff ring wedge, according to an embodiment.

FIG. 7A is a rear view drawing of a cuff ring assembly 100 absent a cuff ring wedge 555, according to an embodiment.

In this view, the locking section 102 of the cuff ring assembly 100 can be viewed clearly, including the locking section opening 702 wherein a cuff ring wedge 555 can be inserted. As the cuff ring assembly comprises a hollow tube, a first opening 712 can be seen in this figure by looking through the locking section opening 702. Additionally, side views of two suture wings 103 as well as a side view of a cuff 130 can also be viewed.

Figure 7B:
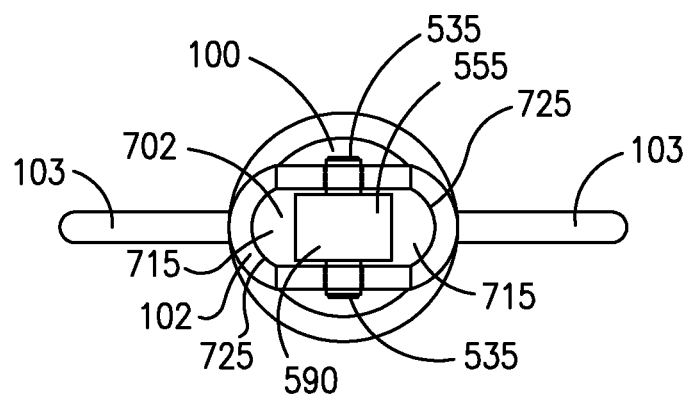
FIG. 7B is a rear view drawing of a cuff ring assembly wherein a cuff ring wedge has been connected to the locking section, according to an embodiment.

FIG. 7B is a rear view drawing of a cuff ring assembly 100 wherein a cuff ring wedge 555 has been connected to the locking section 102 of the cuff ring assembly 100, according to an embodiment. The back side 590 of the cuff ring wedge 555, discussed in detail above with reference to FIG. 5B, can be viewed in this figure.

In an embodiment, when a cuff ring wedge 555 has been connected to the locking section 102 within a locking section opening 702, D-shaped spaces 715 can be created on either side of the cuff ring wedge 555, which can be configured to each allow a trailing limb of a dual-lumen hemodialysis catheter (not shown in FIG. 7B) to pass through them. In an embodiment, the size and shape of the cuff ring wedge 555 can be sufficient to press each trailing limb (not shown in FIG. 7B) against the outside inner-wall 725 of the locking section 102, thus securing the trailing limbs to the locking section 102 and the cuff ring assembly 100, while still allowing fluids to pass through the trailing limbs.

FIG. 8 is a perspective view drawing showing the rear, top and side of a cuff ring assembly 100, according to an embodiment. This view depicts the locations of two cuff ring wedge mounting holes 125 and 126 within the locking section 102 and the locking section opening 702 in an embodiment.

Figure 9:
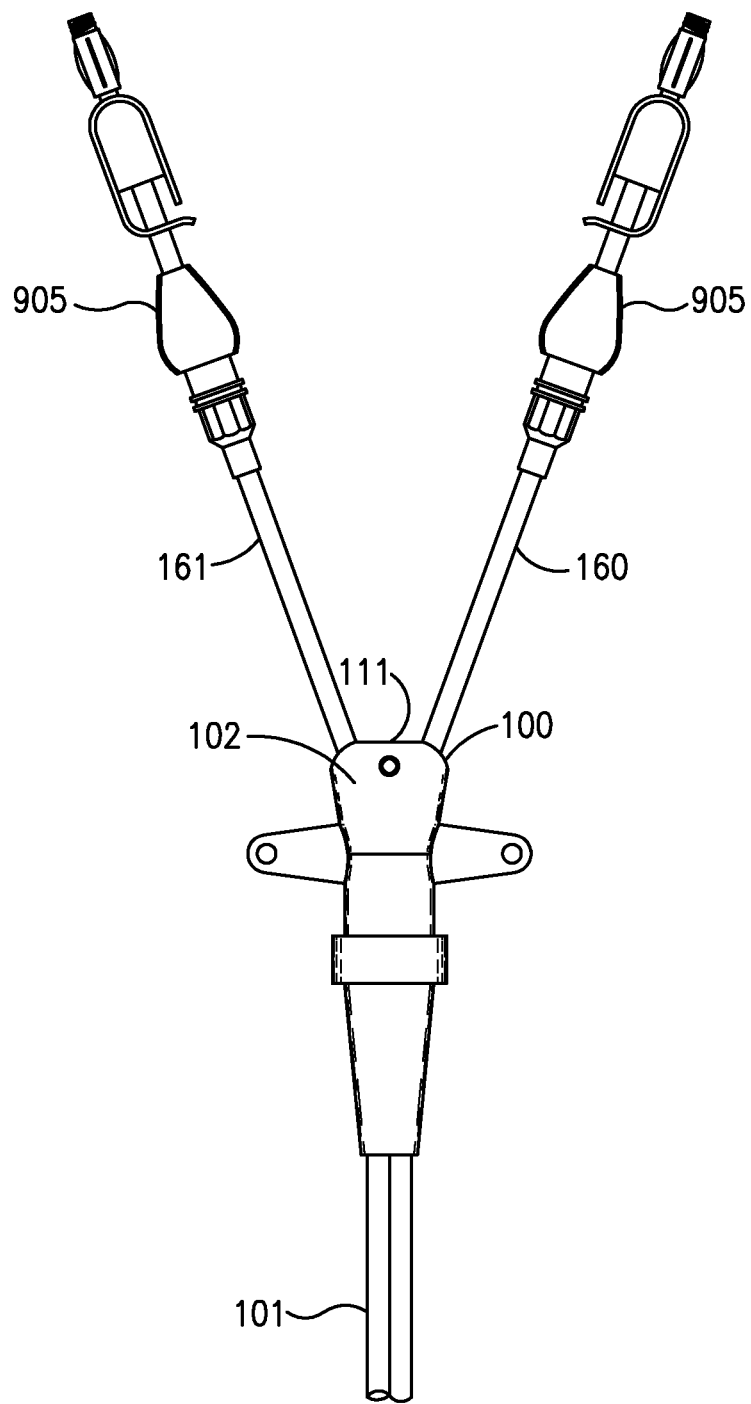
FIG. 9 is a top view drawing of a cuff ring assembly, wherein two trailing limbs of the proximal end of a dual-lumen hemodialysis catheter have been threaded through the cuff ring assembly, and the two trailing limbs have been split apart to a selected location (not visible in FIG. 9) and this location is located within the locking section of the cuff ring assembly and a cuff ring wedge (not visible in FIG. 9) has been placed into the top end of the locking section and between the trailing limbs at the location, thus securing the two trailing limbs to the cuff ring assembly, and wherein the two trailing limbs have been trimmed to the proper length and hub assemblies have been connected to each trailing limb, according to an embodiment.

FIG. 9 is a top view drawing of a cuff ring assembly 100, wherein two trailing limbs 160 and 161 of the dual-lumen hemodialysis catheter 101 have been threaded through the cuff ring assembly 100, and the two trailing limbs 160 and 161 have been split apart to a selected location (not visible in FIG. 9) and this location is located within the locking section 102 of the cuff ring assembly 100 and a cuff ring wedge (not visible in FIG. 9) has been placed into the top end 111 of the locking section 102 and between the trailing limbs 160 and 161 at the location, thus securing the two trailing limbs 160 and 161 to the cuff ring assembly 100, and wherein the two trailing limbs 160 and 161 have been trimmed to the proper length and hub assemblies 905 have been connected to each trailing limb 160 and 161, according to an embodiment.

FIGS. 10A through 10D show four stages (in time sequence) of the of the present tunneled dual-lumen hemodialysis catheter placement.

Figure 10A:
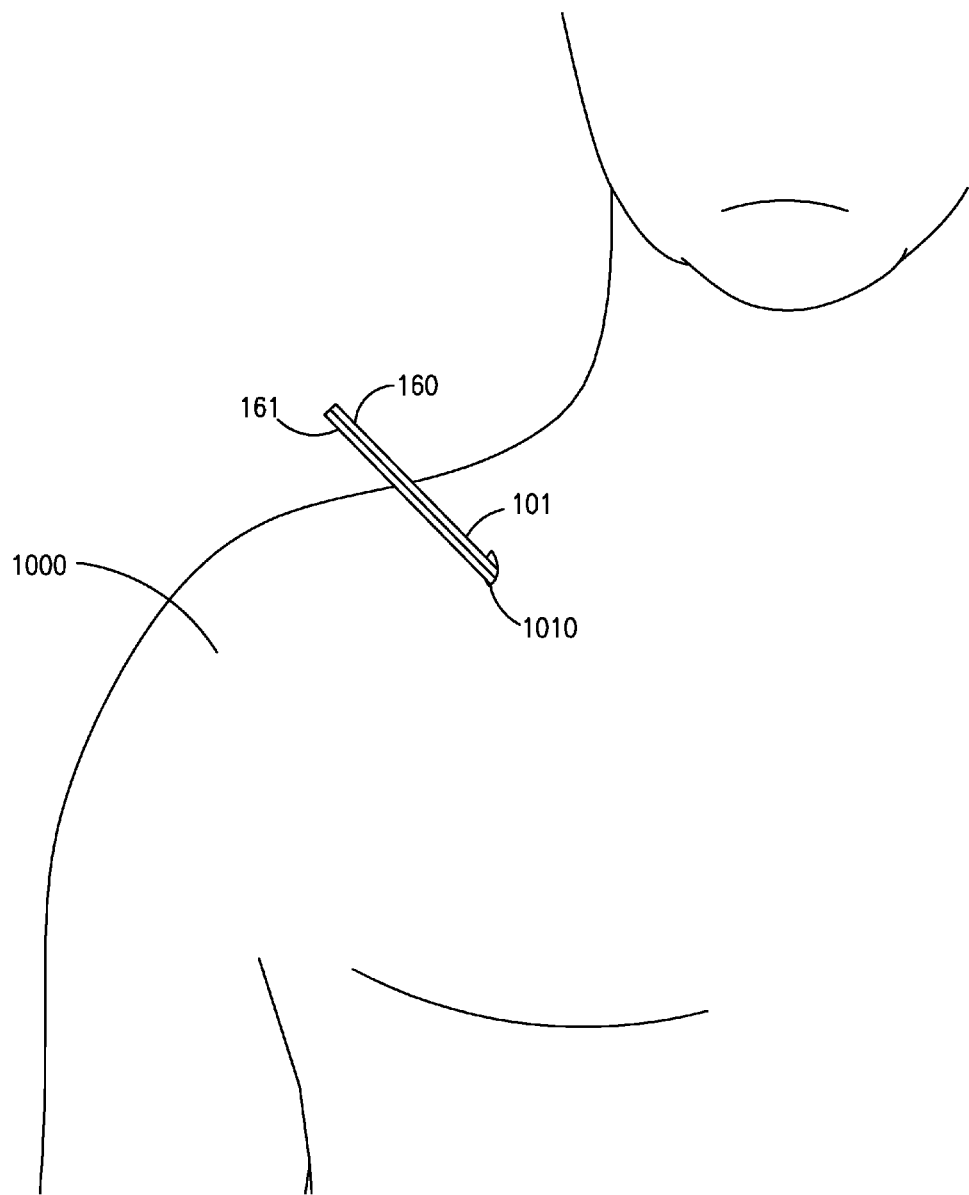
FIG. 10A is a top view drawing of a patient's upper torso, wherein the trailing limbs of the proximal end of a dual-lumen hemodialysis catheter extend from an incision in the patient's chest located at one end of a subcutaneous tunnel (not visible in FIG. 10A), according to an embodiment.

FIG. 10A is a top view drawing of a patient's upper torso 1000, wherein the trailing limbs 160 and 161 of the dual-lumen hemodialysis catheter 101 extend from an incision 1010 in the patient's chest located at one end of a subcutaneous tunnel (not visible), according to an embodiment.

In an embodiment, a surgeon can use a tunneler or similar device to position the leading (distal) end of a dual-lumen hemodialysis catheter 101 within a large vein in the patient's upper torso 1000, usually the superior vena cava. The surgeon can then use a tunneler or similar device to retrograde tunnel the trailing limbs 160 and 161 back through a subcutaneous tract where they can be placed through a skin exit site, typically an incision created with a scalpel, which can be located on the surface of the patient's upper torso 1000.

Figure 10B:
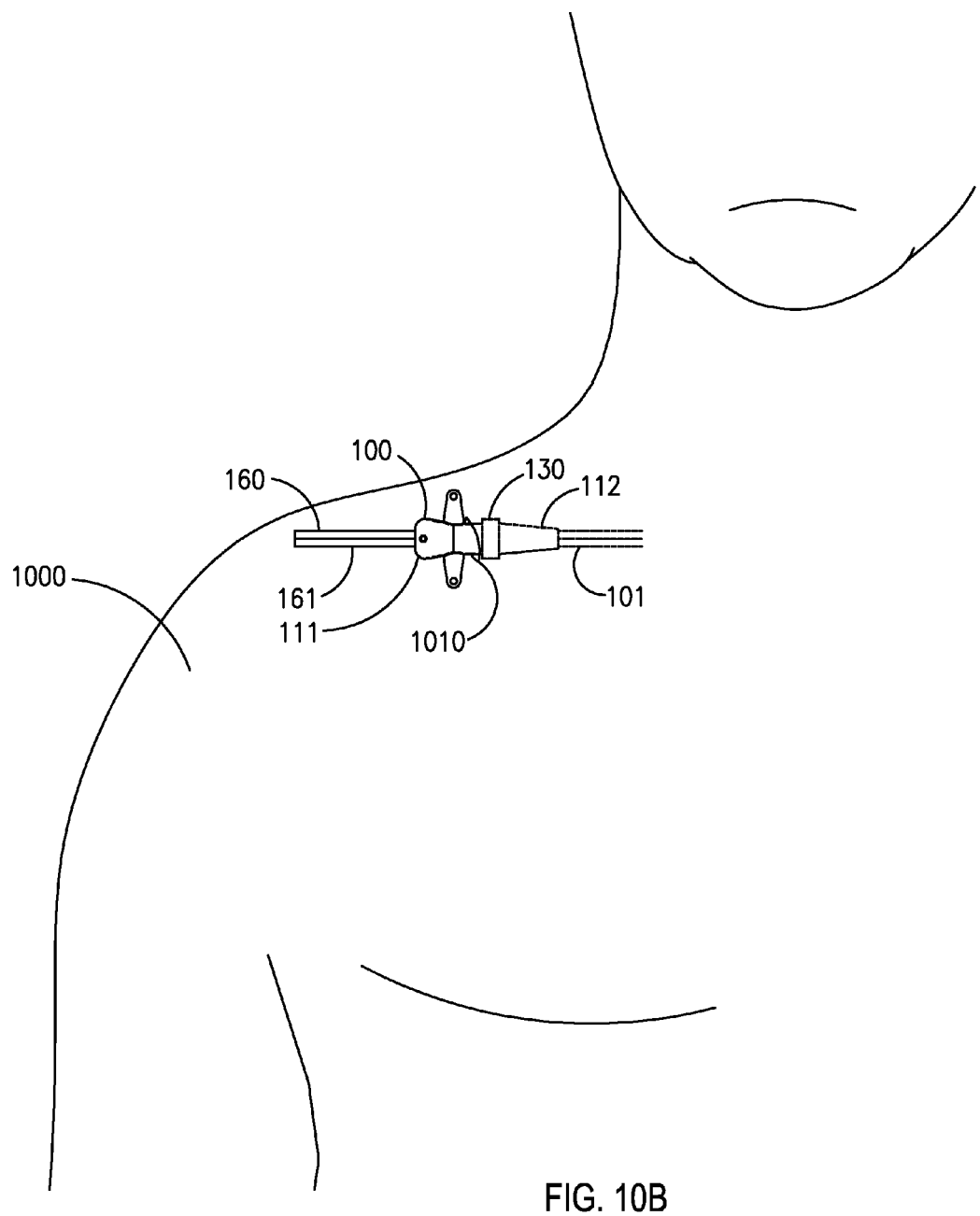
FIG. 10B is a top view drawing of a patient's upper torso, wherein the trailing limbs of the proximal end of a dual-lumen hemodialysis catheter extend from an incision in the patient's chest and the trailing limbs have been threaded through the cuff ring assembly so that the trailing limbs extend through a top end of the cuff ring assembly and a cuff has been used to close the incision over a bottom end of the cuff ring assembly and the cuff has been positioned within a subcutaneous tunnel (not visible in FIG. 10B), according to an embodiment.

FIG. 10B is a top view drawing of a patient's upper torso 1000, wherein the trailing limbs 160 and 161 of the dual-lumen hemodialysis catheter 101 extend from an incision 1010 in the patient's chest and the trailing limbs 160 and 161 have been threaded through the cuff ring assembly 100 so that the trailing limbs 160 and 161 extend through a top end 111 of the cuff ring assembly 100 and a cuff 130 has been used to close the incision 1010 over a bottom end 112 of the cuff ring assembly 100 and the cuff 130 has been positioned within a subcutaneous tunnel (not visible), according to an embodiment. (The parts of the cuff ring assembly 100 and dual-lumen hemodialysis catheter 101 shown in broken lines in FIGS. 10B thru 10D are located below the patient's skin and are not visible.)

In an embodiment, a surgeon or other user can then place the cuff ring assembly over the trailing limbs 160 and 161 dual-lumen hemodialysis catheter 101 by threading the trailing limbs 160 and 161, comprising the proximal end of the hemodialysis catheter, 101 into the first opening (not visible in FIG. 10B) located at the bottom end 112 of the cuff ring assembly 100 and out from the second opening (not visible in FIG. 10B) located at the top end 111 of the cuff ring assembly 100. In an embodiment, a surgeon or other user can position the cuff 130 within the subcutaneous tunnel through the incision 1010 in order to close and seal the incision 1010 to prevent infection.

Figure 10C:
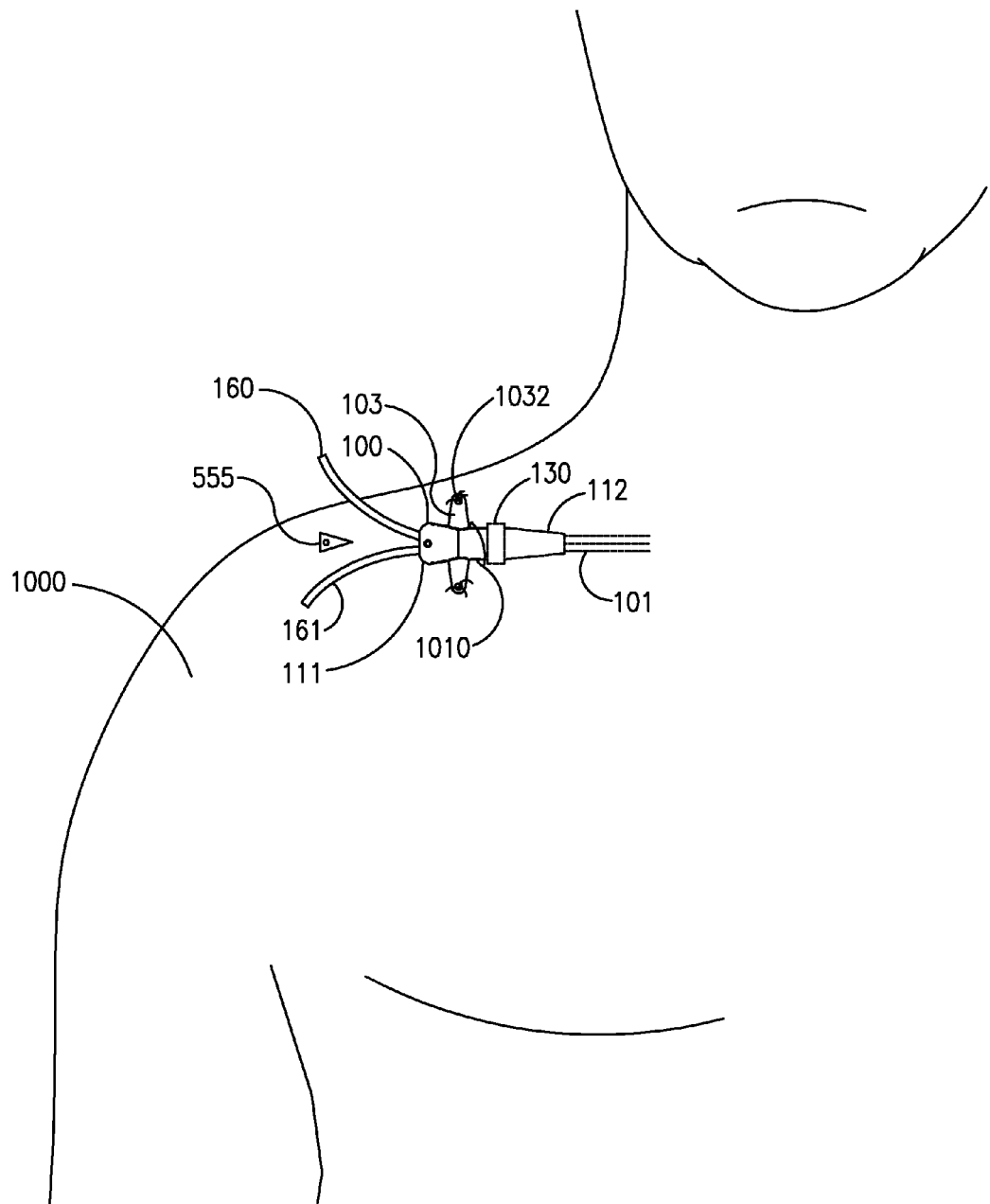
FIG. 10C is a top view drawing of a patient's upper torso, wherein the trailing limbs of the proximal end of a dual-lumen hemodialysis catheter extend from an incision in the patient's chest and the trailing limbs have been threaded through the cuff ring assembly so that the trailing limbs extend through a top end of the cuff ring assembly and a cuff has been used to close the incision over a bottom end of the cuff ring assembly and the cuff has been positioned within a subcutaneous tunnel (not visible in FIG. 10C) and the trailing limbs have been split apart down to a selected position within the cuff ring assembly, according to an embodiment.
Figure 10D:
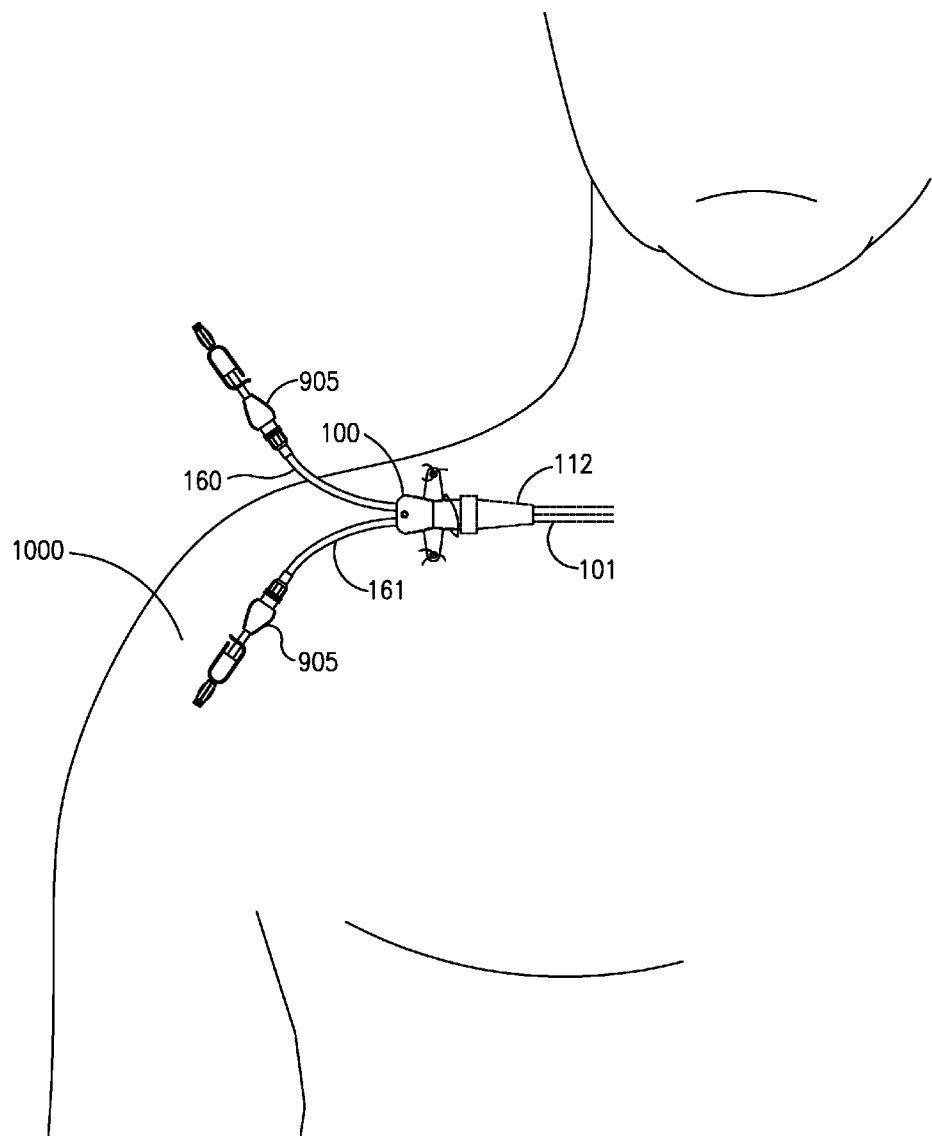
FIG. 10D is a top view drawing of a patient's upper torso, wherein the trailing limbs of the proximal end of a dual-lumen hemodialysis catheter extend from an incision in the patient's chest and the trailing limbs have been threaded through the cuff ring assembly so that the trailing limbs extend through a top end of the cuff ring assembly and a cuff has been used to close the incision over a bottom end of the cuff ring assembly and its trailing limbs have been split apart down to a selected position within the cuff ring assembly and a cuff ring wedge has been connected to the cuff ring assembly to secure the trailing limbs to the cuff ring assembly, and a hub assembly has been connected to each trailing limb, according to an embodiment.

FIG. 10C is a top view drawing of a patient's upper torso 1000, wherein the trailing limbs 160 and 161 of the dual-lumen hemodialysis catheter 101 extend from an incision 1010 in the patient's chest and the trailing limbs 160 and 161 have been threaded through the cuff ring assembly 100 so that the trailing limbs 160 and 161 extend through a top end 111 of the cuff ring assembly 100 and a cuff 130 has been used to close the incision 1010 over a bottom end 112 of the cuff ring assembly 100 and the cuff 130 has been positioned within a subcutaneous tunnel (not visible) and the trailing limbs 160 and 161 have been split apart down a selected point to the cuff ring assembly 100, according to an embodiment. The trailing limbs 160 and 161 can be trimmed to the desired length with scissors or any other suitable cutting tool.

In an embodiment, after the cuff ring assembly 100 has been positioned over the trailing limbs 160 and 161, a user can then split apart the trailing limbs 160 and 161 to a selected point within the top end 111 of the cuff ring assembly 100 and trim the trailing limbs 160 and 161 to a desired length. In an embodiment, the trailing limbs 160 and 161 can be configured so that they can be pulled apart by hand. Also shown in FIG. 10C, the user can secure the cuff ring assembly 100 to the patient's upper torso 1000 by connecting one or more suture wings 103 to the patient's skin with sutures 1032.

In an embodiment, a user can secure the trailing limbs 160 and 161 to the top end 111 of the cuff ring assembly 100 by placing a cuff ring wedge 555 within the top end 111 and between the trailing limbs 160 and 161.

FIG. 10D is a top view drawing of a patient's upper torso 1000 wherein the trailing limbs 160 and 161 of the dual-lumen hemodialysis catheter 101 extend from an incision 1010 in the patient's chest and the trailing limbs 160 and 161 have been threaded through the cuff ring assembly 100 so that the trailing limbs 160 and 161 extend through a top end 111 of the cuff ring assembly 100 and a cuff 130 (not numbered in FIG. 10D) has been used to close the incision 1010 (not numbered in FIG. 10D) over a bottom end 112 of the cuff ring assembly 100 and its trailing limbs 160 and 161 have been split apart down to a selected position within the cuff ring assembly 100 and a cuff ring wedge 555 (not visible in FIG. 10D) has been connected to the cuff ring assembly 100 to secure the trailing limbs 160 and 161 to the cuff ring assembly 100, and hub assemblies 905 have been connected to each trailing limb 160 and 161, according to an embodiment.

In an embodiment, the user can connect a hub assembly 905 to each trailing limb 160 or 161. These hub assemblies 905 allow additional tubing (not shown), which can be required to perform hemodialysis, to be connected to the present dual-lumen hemodialysis catheter 101. A standard hub assembly 905 can also have the ability to prevent the flow of liquids either into or out from the present dual-lumen hemodialysis catheter 101.

The cuff ring assembly 100 can be made in total or in part from various plastics or similar suitable materials, known in the art of medical devices.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention. If any portion of any component of the invention is not shown in the figures taken in their entirety, then absent any written description to the contrary it can be assumed that such portion matches corresponding visible/described portions of the component. The inventive concept includes all methods of using all or any combination of the features described herein, including the methods illustrated in sequence from FIGS. 10A to 10D and their accompanying description.

What is claimed is:

1. A cuff ring assembly for use with a dual-lumen hemodialysis catheter comprising:
a cuff ring comprising a hollow tube having a bottom end and a top end, wherein the bottom end comprises a first opening and the top end comprises a locking section opening and the cuff ring is configured to allow a proximal end of a dual-lumen hemodialysis catheter, comprising a first trailing limb and a second trailing limb, to pass into the cuff ring through the first opening and exit from the cuff ring through the locking section opening;

the top end further comprising a locking section configured to receive a cuff ring wedge through the locking section opening, wherein the cuff ring wedge is configured to be connected within the locking section and wherein the cuff ring wedge, when connected within the locking section, creates a first limb opening located between the cuff ring wedge and the locking section, which is configured to allow the first trailing limb to pass through the first limb opening, and wherein the first trailing limb is secured to the cuff ring when it is placed within the first limb opening and the cuff ring wedge is connected to the locking section; and a cuff configured to be placed over the bottom end of the cuff ring.

2. A cuff ring assembly for use with a dual-lumen hemodialysis catheter comprising:
a cuff ring comprising a hollow tube having a bottom end and a top end, wherein the bottom end comprises a first opening and the top end comprises a locking section opening and the cuff ring is configured to allow a proximal end of a dual-lumen hemodialysis catheter, comprising a first trailing limb and a second trailing limb, to pass into the cuff ring through the first opening and exit from the cuff ring through the locking section opening;

the top end further comprising a locking section configured to receive a cuff ring wedge through the locking section opening, wherein the cuff ring wedge is configured to be connected within the locking section and wherein the cuff ring wedge, when connected within the locking section, creates a second limb opening, located between the cuff ring wedge and the locking section, which is configured to allow the second trailing limb to pass through the second limb opening, and wherein the second trailing limb is secured to the cuff ring when it is placed within the second limb opening and the cuff ring wedge is connected to the locking section; and a cuff configured to be placed over the bottom end of the cuff ring.

3. A cuff ring assembly for use with a dual-lumen hemodialysis catheter comprising:
a cuff ring comprising a hollow tube having a bottom end and a top end, wherein the bottom end comprises a first opening and the top end comprises a locking section opening and the cuff ring is configured to allow a proximal end of a dual-lumen hemodialysis catheter, comprising a first trailing limb and a second trailing limb, to pass into the cuff ring through the first opening and exit from the cuff ring through the locking section opening;

the top end further comprising a locking section configured to receive a cuff ring wedge through the locking section opening, wherein the cuff ring wedge is configured to be connected within the locking section and wherein the cuff ring wedge comprises one or more cuff ring wedge pegs and the locking section comprises one or more cuff ring wedge-mounting holes, each configured to receive a cuff ring wedge peg; and a cuff configured to be placed over the bottom end of the cuff ring.

4. A dual-lumen hemodialysis catheter apparatus comprising:

a dual-lumen hemodialysis catheter comprising a distal end and a proximal end, wherein the proximal end comprises a first trailing limb and a second trailing limb;

a cuff ring assembly further comprising a cuff ring comprising a hollow tube having a bottom end and a top end, wherein the bottom end comprises a first opening and the top end comprises a locking section opening and the cuff ring is configured to allow the proximal end of the dual-lumen hemodialysis catheter to pass into the cuff ring through the first opening and exit from the cuff ring through the locking section opening, wherein the top end of the cuff ring further comprises a locking section configured to receive a cuff ring wedge through the locking section opening, and wherein the cuff ring wedge is configured to be connected within the locking section and wherein the cuff ring wedge, when connected within the locking section, creates a first limb opening located between the cuff ring wedge and the locking section, which is configured to allow the first trailing limb to pass through the first limb opening, and wherein the first trailing limb is secured to the cuff ring when it is placed within the first limb opening and the cuff ring wedge is connected to the locking section; and a cuff configured to be placed over the bottom end of the cuff ring.

5. A dual-lumen hemodialysis catheter apparatus comprising:

a dual-lumen hemodialysis catheter comprising a distal end and a proximal end, wherein the proximal end comprises a first trailing limb and a second trailing limb;

a cuff ring assembly further comprising a cuff ring comprising a hollow tube having a bottom end and a top end, wherein the bottom end comprises a first opening and the top end comprises a locking section opening and the cuff ring is configured to allow the proximal end of the dual-lumen hemodialysis catheter to pass into the cuff ring through the first opening and exit from the cuff ring through the locking section opening, wherein the top end of the cuff ring further comprises a locking section configured to receive a cuff ring wedge through the locking section opening, and wherein the cuff ring wedge is configured to be connected within the locking section and wherein the cuff ring wedge, when connected within the locking section, creates a second limb opening, located between the cuff ring wedge and the locking section, which is configured to allow the second trailing limb to pass through the second limb opening, and wherein the second trailing limb is secured to the cuff ring when it is placed within the second limb opening and the cuff ring wedge is connected to the locking section; and a cuff configured to be placed over the bottom end of the cuff ring.

6. A dual-lumen hemodialysis catheter apparatus comprising:

a dual-lumen hemodialysis catheter comprising a distal end and a proximal end, wherein the proximal end comprises a first trailing limb and a second trailing limb;

a cuff ring assembly further comprising a cuff ring comprising a hollow tube having a bottom end and a top end, wherein the bottom end comprises a first opening and the top end comprises a locking section opening and the cuff ring is configured to allow the proximal end of the dual-lumen hemodialysis catheter to pass into the cuff ring through the first opening and exit from the cuff ring through the locking section opening, wherein the top end of the cuff ring further comprises a locking section configured to receive a cuff ring wedge through the locking section opening, and wherein the cuff ring wedge is configured to be connected within the locking section and wherein the cuff ring wedge comprises one or more cuff ring wedge pegs and the locking section comprises one or more cuff ring wedge-mounting holes, each configured to receive a cuff ring wedge peg; and a cuff configured to be placed over the bottom end of the cuff ring.

* * * * *